US009162040B2

(12) United States Patent
Vo et al.

(10) Patent No.: US 9,162,040 B2
(45) Date of Patent: Oct. 20, 2015

(54) BALLOON CATHETER AND METHOD OF USE

(71) Applicants: Stryker Corporation, Kalamazoo, MI (US); Stryker NV Operations Limited, Dublin (IE)

(72) Inventors: Justin T. Vo, San Jose, CA (US); Jon Schabert, Dublin, CA (US)

(73) Assignees: STRYKER CORPORATION, Kalamazoo, MI (US); STRYKER EUROPEAN HOLDINGS I, LLC, Kalamazoo, MI (US)

( * ) Notice: Subject to any disclaimer, the term of this patent is extended or adjusted under 35 U.S.C. 154(b) by 277 days.

(21) Appl. No.: 13/722,948

(22) Filed: Dec. 20, 2012

(65) Prior Publication Data

US 2013/0184644 A1     Jul. 18, 2013

Related U.S. Application Data

(63) Continuation-in-part of application No. 13/413,486, filed on Mar. 6, 2012, now Pat. No. 8,585,643.

(60) Provisional application No. 61/449,996, filed on Mar. 7, 2011.

(51) Int. Cl.
*A61M 31/00* (2006.01)
*A61M 25/10* (2013.01)
(Continued)

(52) U.S. Cl.
CPC ............. *A61M 25/10* (2013.01); *A61M 25/005* (2013.01); *A61M 25/0053* (2013.01);
(Continued)

(58) Field of Classification Search
CPC ..................... A61M 25/10; A61M 2025/0059; A61M 25/005; A61M 25/0053; A61M 25/0054; A61M 25/0138; A61M 2025/09133; A61M 25/0013; A61M 25/0043; A61M 25/0051; A61M 25/0144; A61M 2025/0681; A61M 2025/1063; A61M 25/0012; B26D 3/16; Y10T 29/49826; A61F 2/958
USPC ........................................................ 604/103.09
See application file for complete search history.

(56) References Cited

U.S. PATENT DOCUMENTS 5,106,455 A    4/1992 Jacobsen et al.
5,238,004 A    8/1993 Sahatjian et al.
(Continued)

FOREIGN PATENT DOCUMENTS

WO    2006135964    12/2006

OTHER PUBLICATIONS

PCT International Search Report and Written Opinion for PCT/US2012/027910, Applicant Stryker Corporation forms PC/ISA/210, 220, and 237, dated May 18, 2012 (15 pages).

*Primary Examiner* — Jason Flick
(74) *Attorney, Agent, or Firm* — Vista IP Law Group LLP

(57) ABSTRACT

A balloon catheter includes an elongate support member defining first and second openings therein, open proximal and distal ends, and an axial lumen; and a balloon disposed on the elongate support member, the balloon defining a balloon interior through which the support member extends, where the balloon interior has a proximal end region, a middle region, and a distal end region, with the first opening located in the middle region, and the second opening located in the distal end region, such that the support member lumen is in communication with the balloon interior through each of the first and second openings, and such that a pressurized liquid introduced through the open proximal end of the support member will enter the balloon interior through the first opening, and subsequently exit the balloon interior through the second opening, back into the lumen, and out the open distal end of the support member.

16 Claims, 15 Drawing Sheets

(51) Int. Cl.
  *A61M 25/00*  (2006.01)
  *B26D 3/16*  (2006.01)

(52) U.S. Cl.
  CPC ............ *A61M 25/0054* (2013.01); *B26D 3/16* (2013.01); *A61M 2025/0059* (2013.01); *Y10T 29/49826* (2015.01); *Y10T 83/0304* (2015.04)

(56) References Cited

U.S. PATENT DOCUMENTS

| | | | |
|---|---|---|---|
| 5,772,609 A | 6/1998 | Nguyen et al. | |
| 6,139,510 A | 10/2000 | Palermo | |
| 6,508,803 B1 | 1/2003 | Horikawa et al. | |
| 6,579,246 B2 | 6/2003 | Jacobsen et al. | |
| 6,766,720 B1 | 7/2004 | Jacobsen et al. | |
| 6,918,882 B2 | 7/2005 | Skujins et al. | |
| 7,071,197 B2 | 7/2006 | Leonardi et al. | |
| 7,878,984 B2 | 2/2011 | Jacobsen et al. | |
| 2002/0082585 A1 | 6/2002 | Carroll et al. | |
| 2003/0069522 A1 | 4/2003 | Jacobsen et al. | |
| 2004/0181174 A2 | 9/2004 | Davis et al. | |
| 2005/0197668 A1* | 9/2005 | Lim et al. | 606/194 |
| 2006/0122537 A1 | 6/2006 | Reynolds et al. | |
| 2007/0083132 A1 | 4/2007 | Sharrow | |
| 2007/0135763 A1* | 6/2007 | Musbach et al. | 604/96.01 |
| 2009/0156999 A1 | 6/2009 | Adams | |

* cited by examiner

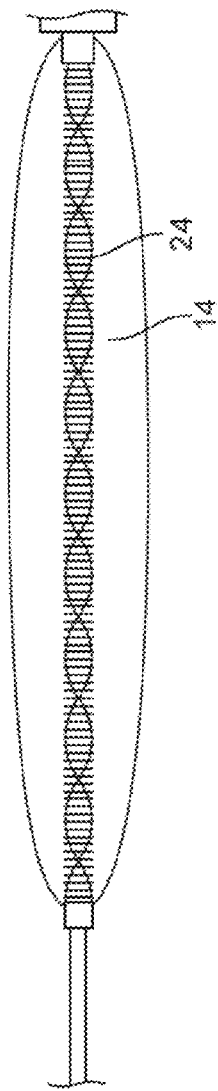
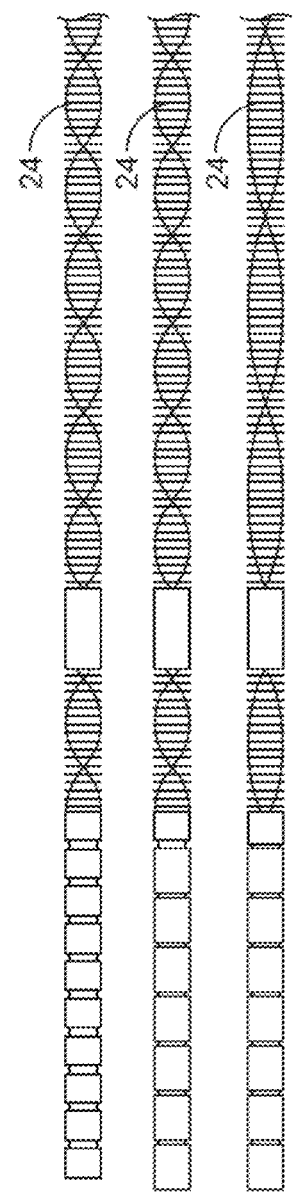
FIG. 3A
FIG. 3B

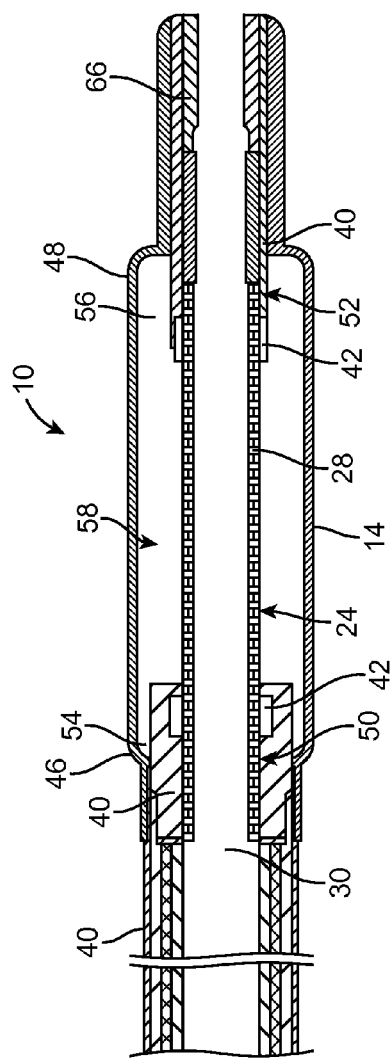
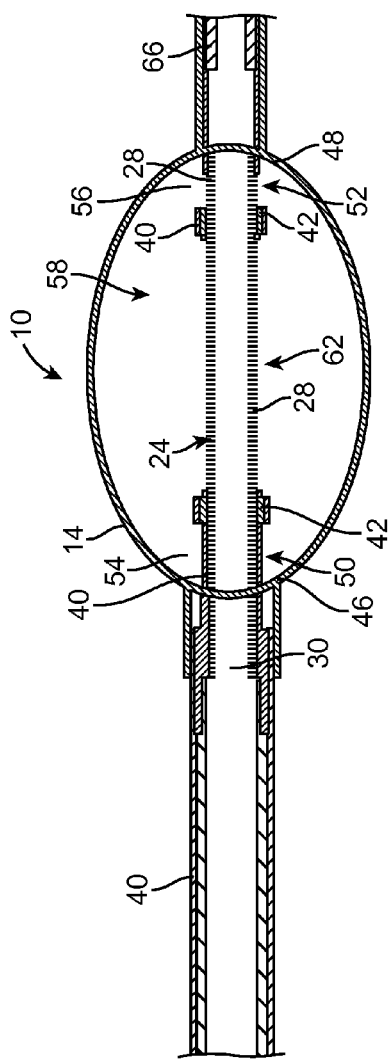
FIG. 15
FIG. 16

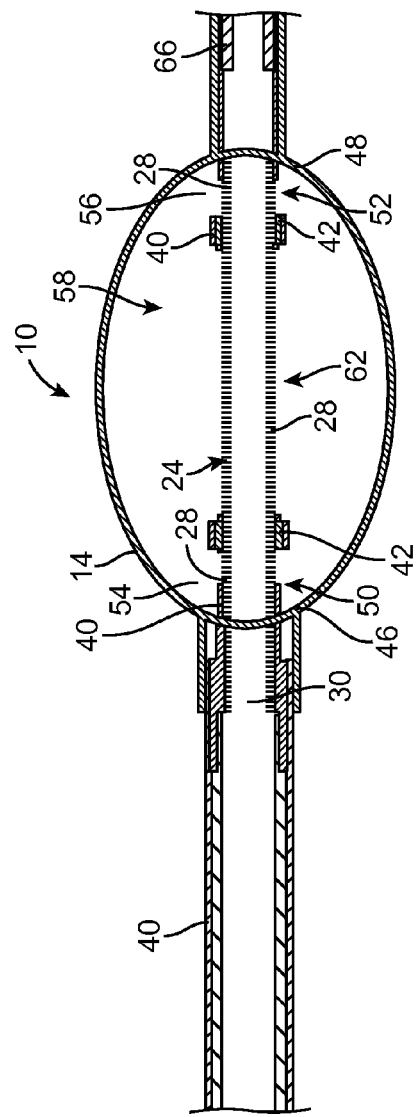
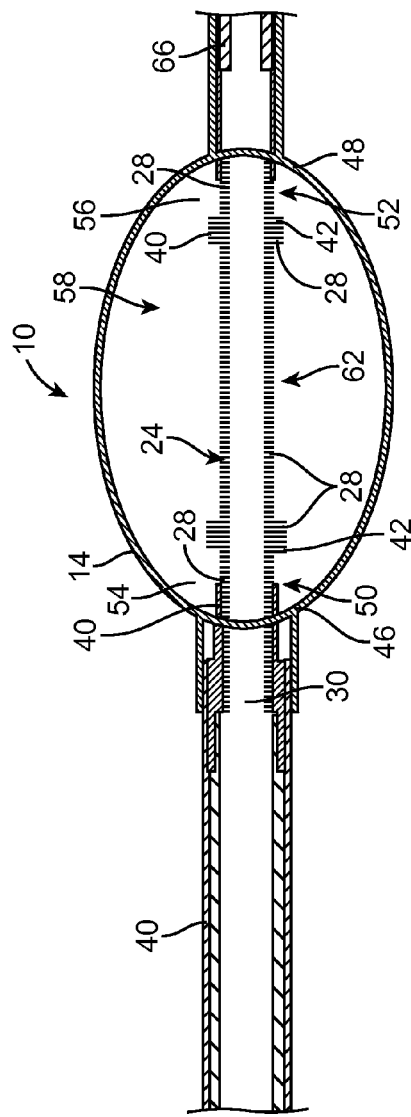

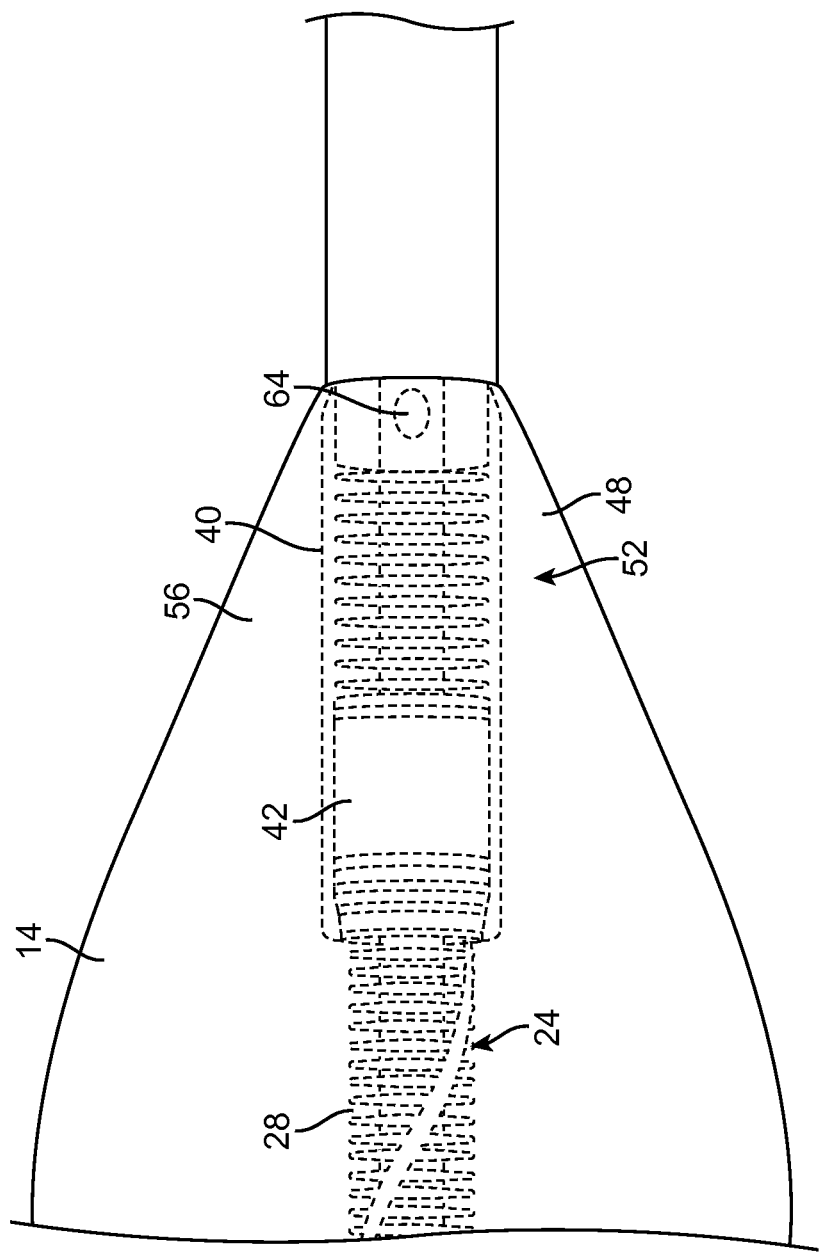

BALLOON CATHETER AND METHOD OF USE

RELATED APPLICATION DATA

The present application is a continuation-in-part of application Ser. No. 13/413,486, filed Mar. 6, 2012, which claims the benefit under 35 U.S.C. §119 to U.S. Provisional Application No. 61/449,996, filed Mar. 7, 2011, the entire contents of both of which are incorporated herein by reference as though set forth in full.

FIELD

The present disclosure relates generally to medical devices and methods of manufacturing such devices. More particularly, the present disclosure relates to balloon catheters and balloon catheter support shafts.

BACKGROUND

The use of intravascular medical devices has become an effective method for treating many types of vascular disease. In general, a suitable intravascular device is inserted into the vascular system of the patient and navigated through the vasculature to a desired target site. Using this method, virtually any target site in the patient's vascular system may be accessed, including the coronary, cerebral, and peripheral vasculature.

Catheters are often utilized to place medical devices such as stents and embolic devices at a desired location within the body. A medical prosthesis, such as a stent for example, may be loaded onto a catheter in a configuration having a reduced diameter and then introduced into the lumen of a body vessel. Once delivered to a target location within the body, the stent may then be expanded to an enlarged configuration within the vessel to support and reinforce the vessel wall while maintaining the vessel in an open, unobstructed condition. The stent may be configured to be self-expanding, expanded by an internal radial force such as a balloon, or a combination of self-expanding and balloon expandable.

Balloon catheters are used in a number of endovascular applications including temporarily or permanently occluding blood flow either distal or proximal of a treatment site during neurological examinations, delivering diagnostic agents such as contrast media, assisting in neurovascular embolic coiling of an aneurysm or arteriovenous malformation (AVM), and dilating narrowed blood vessels caused by vasospasm. During therapeutic procedures such as the ones mentioned above, fast aspiration-mediated deflation of the balloon catheter quickly restores sufficient or normal blood flow to the brain in order to avoid potential neurological impairment, such as weakness, loss of sensation, speech problems, etc.

Current single lumen balloon catheters have a few inflation/deflation ports either punched or laser drilled in the polymeric elongated distal shaft. An inadequate seal between the balloon distal tip and the guidewire may lead to blood entering the balloon, which may result in poor balloon visibility and clot formation around the inflation/deflation ports. In an emergency involving a balloon catheter, a physician may be forced to "bail out" by withdrawing the guidewire proximally away from the balloon to instantly deflate the balloon to restore blood flow to the brain. Poor balloon visibility and inability to quickly deflate the balloon during a procedure could lead to vessel damage and other serious complications.

In preparation for use, balloon catheters are flushed with fluid, such as saline. This fluid can be introduced using a syringe connected to a hub, such as a Luer fitting with a rotary selector valve. Air in these parts can be introduced as air bubbles into the balloon catheter during flushing. The difference between the outer diameter of the balloon support member and the inner diameter of the balloon results in the formation of an annular space and air bubble entrapment in the balloon catheter during flushing. Air bubble entrapment is especially problematic in larger diameter compliant and super compliant balloons.

Due to the pressure differential along the longitudinal axis of the balloon catheter, many air bubbles collect in the distal end of the balloon. However, with larger diameter balloons, air bubbles may also collect in the proximal end of the balloon. Collected air bubbles can be larger than 1 mm in diameter and may interfere with visualization of the balloon catheter. Further, air bubble may also dislodge from the balloon in vivo, resulting in air embolisms and strokes. Accordingly, after a balloon catheter is flushed during preparation, its balloon is inflated to a nominal diameter and visually inspected to identify any air bubbles above a certain size, e.g., 1 mm. If more than a predetermined number of such air bubbles are identified, the balloon catheter may be "re-prepped" by repeating the cycle of flushing, inflating, and inspecting. However, re-prepping the balloon catheter may expand the dead spaces in the balloon where air bubbles are entrapped, and the dead spaces may retain air bubbles after several cycles of prepping.

A number of different balloon catheters are known, each having certain advantages and disadvantages. However, there is an ongoing need to provide alternative balloon catheters, in particular, alternative balloon catheters that facilitate isotropic bending and rapid deflation, and methods of making such catheters. There is also an ongoing need to provide alternative balloon catheters with reduced air bubble formation during flushing.

SUMMARY

In one embodiment of the disclosed inventions, a balloon catheter comprises an elongate support member comprising a tubular wall defining first and second openings therein, open proximal and distal ends, and an axial lumen in communication with the first and second openings and the open proximal and distal ends; and a balloon disposed on the elongate support member, the balloon defining a balloon interior through which the elongate support member extends, wherein the balloon interior has a proximal end region, a middle region, and a distal end region, with the first opening located in the middle region, and the second opening located in the distal end region, such that the support member lumen is in communication with the balloon interior through each of the first and second openings, and such that a pressurized liquid introduced through the open proximal end of the support member will enter the balloon interior through the first opening, and subsequently exit the balloon interior through the second opening, back into the lumen, and out the open distal end of the support member.

The second opening may be a slot defined by the elongate support member. The balloon catheter may also comprise a radiopaque marker disposed in the balloon interior on the elongate support member between the first opening and the second opening, the radiopaque marker comprising a marker tubular wall or an open pitch coil defining a marker opening therein, wherein the tubular wall of the elongate support member also defines a third opening therein at least partially underlying the marker opening, such that the support member lumen is in communication with the balloon interior through the third opening and the marker opening. The elongate support member may be a metal hypotube, and the first and second openings are micro-machined therein or a polymeric tube, and the first and second openings are drilled therein. The elongate support member may also comprise a polymeric sleeve disposed around a portion of the elongate support member, and wherein the portion of the elongate support member in which the second opening is formed is free of the polymeric sleeve. Alternatively or additionally, the elongate support member may also comprise an annular seal disposed in the lumen distal of the balloon.

In some embodiments of the disclosed inventions, the tubular wall also defines a third opening located in the proximal end region, such that the support member lumen is in communication with the balloon interior through the third opening, and such that a pressurized liquid introduced into the open proximal end of the support member will enter the balloon interior through the first opening, and subsequently exit the balloon interior through the second and third openings, back into the lumen, and out the open distal end of the support member. In such embodiments, the balloon comprises a compliant or super compliant material.

In another embodiment of the disclosed inventions, a balloon catheter comprises an elongate support member comprising a tubular wall defining first, second, and third slot-shaped openings therein, open proximal and distal ends, and an axial lumen in communication with the first, second, and third openings and the open proximal and distal ends; and a balloon disposed on the elongate support member, the balloon defining a balloon interior surrounding a portion of the elongate support member, wherein the balloon interior has a proximal end region, a middle region, and a distal end region, with the first opening located in the middle region, the second opening located in the distal end region, and the third opening located in the proximal end region, such that the support member lumen is in communication with the balloon interior through each of the first, second, and third openings, and such that a pressurized liquid introduced through the open proximal end of the support member will enter the balloon interior through the first opening, and subsequently exit the balloon interior through the second and third openings, back into the lumen, and out the open distal end of the support member.

The balloon catheter may also comprise a radiopaque marker disposed in the balloon interior on the elongate support member between the first opening and the second opening, the radiopaque marker comprising a marker tubular wall or an open pitch coil defining a marker opening therein, wherein the tubular wall of the elongate support member also defines a fourth opening therein at least partially underlying the marker opening, such that the support member lumen is in communication with the balloon interior through the fourth opening and the marker opening. The elongate support member may also comprise a polymeric sleeve disposed around a portion of the elongate support member, and wherein the portions of the elongate support member in which the second and third openings are formed are free of the polymeric sleeve. Alternatively or additionally, the elongate support member may also comprise an annular seal disposed in the lumen distal of the balloon. The balloon may comprise a compliant or super compliant material.

In yet another embodiment of the disclosed inventions, a method of flushing a balloon catheter while minimizing bubble formation, the balloon catheter having a balloon disposed on an elongate support member having a tubular wall, the tubular wall defining first and second openings therein, open proximal and distal ends, and an axial lumen in communication with the first and second openings and the open proximal and distal ends, and the balloon defining a balloon interior through which the elongate balloon extends, wherein the balloon interior has a middle region and a distal end region, with the first opening located in the middle region, and the second opening located in the distal end region, the method comprises the following: (a) introducing a flushing liquid into the lumen through the open proximal end of the support member; and (b) applying a pressure to the flushing liquid such that the flushing liquid will enter the balloon interior through the first opening, and subsequently exit the balloon interior through the second opening, back into the lumen, and out the open distal end of the support member, and such that the flushing liquid will remove at least one air bubble from the balloon interior as the flushing liquid exits the balloon interior.

The method may also comprise the following: (c) inserting a guidewire into the lumen to form a substantially fluid-tight seal with the support member distal of the first and second openings; (d) introducing an inflation liquid into the lumen to at least partially inflate the balloon; and (e) inspecting the inflated balloon to identify air bubbles therein. The method may further comprise the following: (f) removing the guidewire from the lumen to break the substantially fluid-tight seal; (g) allowing the balloon to deflate; and (h) repeating steps (a) to (g) until less than a predetermined minimum number of air bubbles are identified in step (e).

Other and further aspects and features of embodiments of the disclosed inventions will become apparent from the ensuing detailed description in view of the accompanying figures.

BRIEF DESCRIPTION OF THE DRAWINGS

FIG. 2A is a detailed perspective view of the balloon and balloon support shaft of the balloon catheter depicted in FIG. 2.

FIG. 2B is a detailed perspective view of the balloon support shafts according to various embodiments of the invention.

FIG. 2C is a detailed perspective view of the reinforced catheter shaft of the balloon catheter depicted in FIG. 2.

FIG. 3A is a detailed perspective view of a balloon catheter according to one embodiments of the disclosed inventions.

FIG. 3B is a detailed perspective view of various balloon support shafts according to various embodiments of the disclosed inventions.

FIG. 15 is a detailed longitudinal cross-sectional view of the distal portion of a balloon catheter according to one embodiment of the disclosed inventions.

FIG. 16 is a detailed longitudinal cross-sectional view of the distal portion of a balloon catheter according to another embodiment of the disclosed inventions.

FIGS. 19 and 20 are detailed longitudinal cross-sectional views of the distal portions of two balloon catheters according to two different embodiments of the disclosed inventions.

FIGS. 21 and 22 are detailed side schematic views of the distal portion of a balloon catheter according to yet another embodiment of the disclosed inventions.

DETAILED DESCRIPTION OF THE ILLUSTRATED EMBODIMENTS

Figure 1:
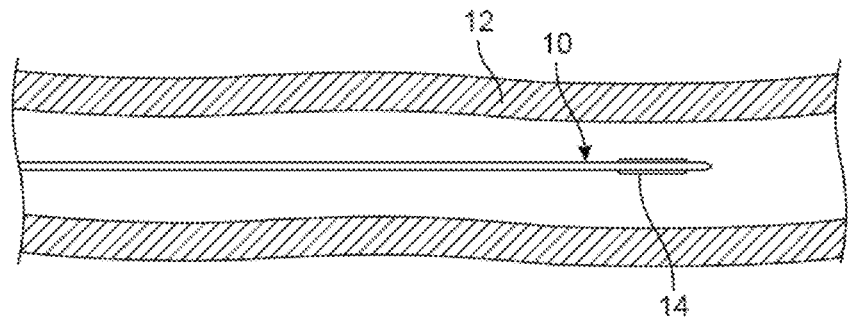
FIG. 1 is a plan view of a balloon catheter constructed according to one embodiment of the disclosed inventions and disposed in a vessel.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

FIG. 1 is a plan view of a balloon catheter 10 disposed in a blood vessel 12. Balloon catheter 10 includes a balloon 14 configured to expand to seal vessels 12 within the anatomy of a patient. Balloon catheter 10 may be used for intravascular procedures. For example, balloon catheter 10 may be used in conjunction with other medical devices, such as a stent or a vaso-occlusive device, to treat and/or diagnose a medical condition.

Figure 2:
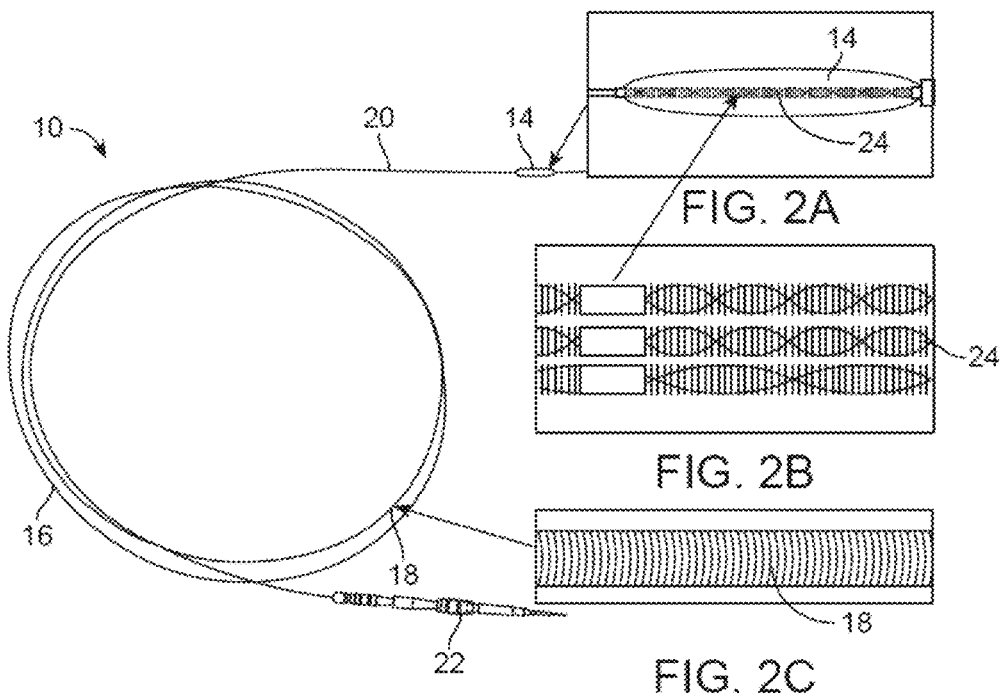
FIG. 2 is a perspective view of a balloon catheter constructed according to one embodiment of the disclosed inventions, including insets showing the catheter shaft, the balloon and various balloon support shafts.

FIG. 2 shows a balloon catheter 10 including an elongate member 16 having a proximal portion 18 and a distal portion 20. In FIG. 2, much of the proximal portion 18 is wound into a loop to display the entire catheter shaft design. An inflation source 22, such as a 1 cc or 3 cc syringe 22, is attached to the elongate member 16 at its proximal end using a three-way stopcock. A balloon 14 is attached to the distal end of the elongate member 16. The balloon 14 is also shown in an inset (2a) in sufficient detail to display the balloon support shaft 24 in the distal portion 20 of the elongate member 16. A second inset (2b) shows several balloon support shafts 24 according to various embodiments of the inventions. A third inset (2c) shows a reinforced catheter shaft in the proximal portion 18 of the elongate member 16.

FIGS. 3A-8 show various features of the balloon support shaft 24 according to one embodiment of the inventions that will be discussed in greater detail below. As shown in FIGS. 3B, 4, 5, and 7, the balloon support shaft 24 has a tubular member 26 with slots 28 formed therein. When supporting a balloon 14 in a balloon catheter 10, as shown in FIG. 3A, at least a part of the tubular member 26 is disposed inside the balloon 14. The tubular member 26 defines a lumen 30 that accommodates a guidewire (not shown) and provides a fluid path for inflation and deflation of the balloon 14. The structure of the tubular member 26 allows fluid communication between the lumen 30 the balloon 14 through the slots 28. A guidewire seal is provided at the distal end of the balloon 14 to provide a fluid seal about the guidewire. The inflation source 22 is fluidly connected to the lumen 30 into which it can introduce and withdraw inflation fluid and contrast medium. From the proximal opening of the lumen 30, the introduced fluid travels around the guidewire disposed in the lumen 30, through the slots 28, and into the interior of the balloon 14 to facilitate inflation and deflation thereof.

Figure 7:
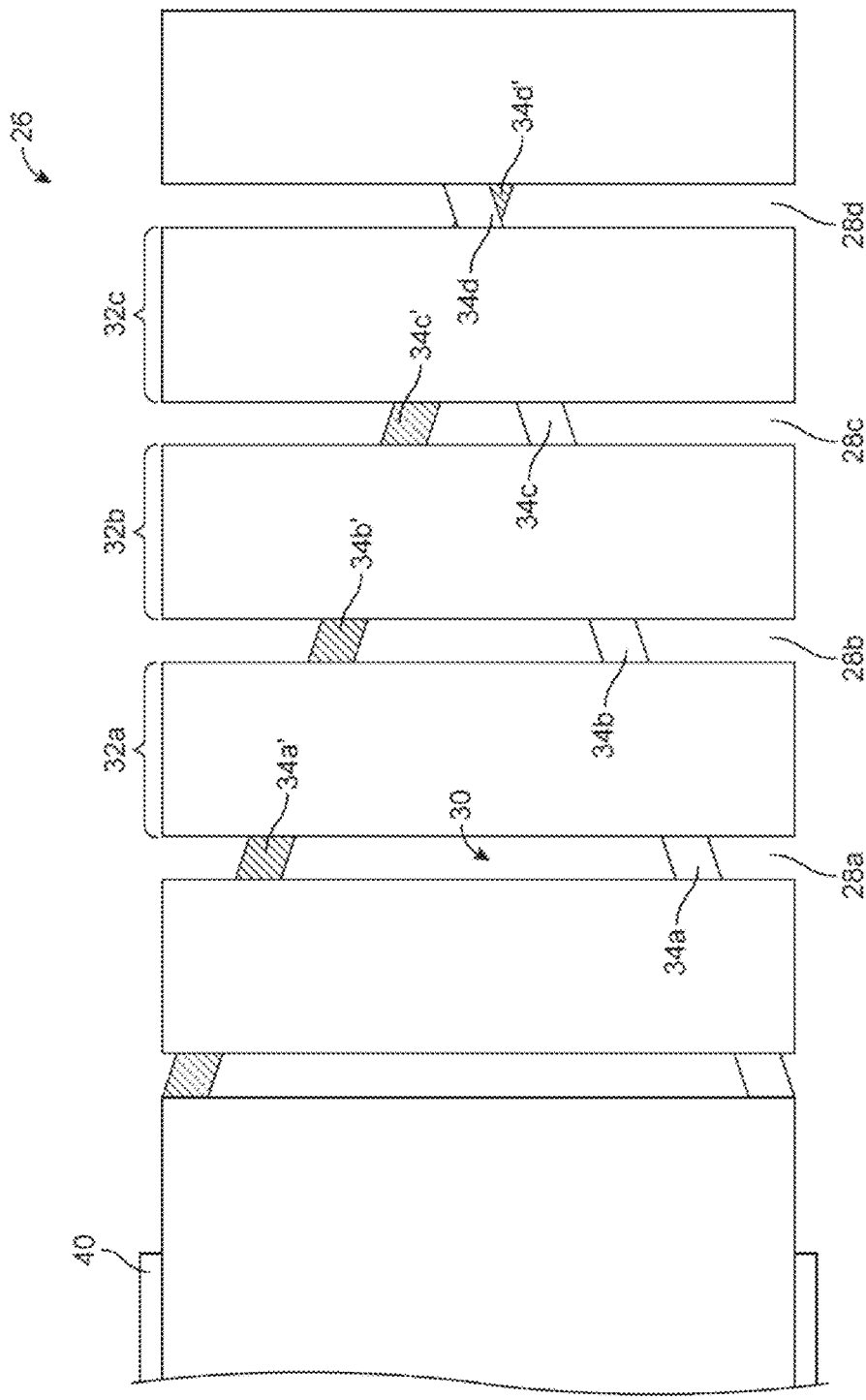
FIG. 7 is a detailed side view of a balloon support shaft constructed according to one embodiment of the disclosed inventions.

FIG. 7 shows the detailed structure of a tubular member 26 according to one embodiment of the inventions. The tubular member 26 is generally a stack of annular segments 32. Tubular member 26 includes a plurality of slots 28 formed therein. Various embodiments of arrangements and configurations of slots 28 are contemplated. In some embodiments, at least some, if not all of slots 28 are disposed at the same or a similar angle with respect to the longitudinal axis of tubular member 26. As shown, slots 28 can be disposed at an angle that is perpendicular, or substantially perpendicular, and/or can be characterized as being disposed in a plane that is normal to the longitudinal axis of tubular member 26. However, in other embodiments, slots 28 can be disposed at an angle that is not perpendicular, and/or can be characterized as being disposed in a plane that is not normal to the longitudinal axis of tubular member 26. Additionally, a group of one or more slots 28 may be disposed at different angles relative to another group of one or more slots 28. The distribution and/or configuration of slots 30 can also include, to the extent applicable, any of those disclosed in U.S. Pat. No. 7,878,984, the entire disclosure of which is herein incorporated by reference.

Slots 28 enhance the flexibility of tubular member 26 while retaining suitable torque transmission characteristics. Slots 28 are formed such that the annular segments 32 are interconnected by one or more beams 34, i.e., the portion of tubular member 26 remaining after slots 28 are formed therein. Such an interconnected structure displays a relatively high degree of torsional stiffness, while retaining a desired level of lateral flexibility. In some embodiments, some adjacent slots 28 can be formed such that they include portions that overlap with each other about the circumference of tubular member 26. In other embodiments, some adjacent slots 28 can be disposed such that they do not necessarily overlap with each other, but are disposed in a pattern that provides the desired degree of lateral flexibility.

Additionally, slots 28 can be arranged along the length of, or about the circumference of, tubular member 26 to achieve desired properties. For example, adjacent slots 28, or groups of slots 28, can be arranged in a symmetrical pattern, such as being disposed essentially equally on opposite sides about the circumference of tubular member 26, or can be rotated by an angle relative to each other about the axis of tubular member 26. Additionally, adjacent slots 28, or groups of slots 28, may be equally spaced along the length of tubular member 26, or can be arranged in an increasing or decreasing density pattern, or can be arranged in a non-symmetric or irregular pattern. Other characteristics, such as slot size, slot shape and/or slot angle with respect to the longitudinal axis of tubular member 26, can also be varied along the length of tubular member 26 in order to vary the flexibility or other properties. In other embodiments, moreover, it is contemplated that the portions of the tubular member may not include any such slots 28.

As suggested above, slots 28 may be formed in groups of two, three, four, five, or more slots 28, which may be located at substantially the same location along the axis of tubular member 26. Alternatively, a single slot 28 may be disposed at some or all of these locations. Within the groups of slots 28, there may be included slots 28 that are equal in size (i.e., span the same circumferential distance around tubular member 26). In some of these as well as other embodiments, at least some slots 28 in a group are unequal in size (i.e., span a different circumferential distance around tubular member 26). Longitudinally adjacent groups of slots 28 may have the same or different configurations.

For example, some embodiments of tubular member 26 include slots 28 that are equal in size in a first group and then unequally sized in an adjacent group. It can be appreciated that in groups that have two slots 28 that are equal in size and are symmetrically disposed around the tube circumference, the centroid of the pair of beams 34 is coincident with the central axis of tubular member 26. Conversely, in groups that have two slots 28 that are unequal in size and whose beams 34 are directly opposed on the tube circumference, the centroid of the pair of beams 34 is offset from the central axis of tubular member 26. Some embodiments of tubular member 26 include only slot groups with centroids that are coincident with the central axis of the tubular member 26, only slot groups with centroids that are offset from the central axis of tubular member 26, or slot groups with centroids that are coincident with the central axis of tubular member 26 in a first group and offset from the central axis of tubular member 26 in another group. The amount of offset may vary depending on the depth (or length) of slots 28 and can include essentially any suitable distance.

Slots 28 can be formed by methods such as micro-machining, saw-cutting (e.g., using a diamond grit embedded semiconductor dicing blade), electron discharge machining, grinding, milling, casting, molding, chemically etching or treating, or other known methods, and the like. In some such embodiments, the structure of the tubular member 26 is formed by cutting and/or removing portions of the tube to form slots 28. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing balloon catheter 10 may include forming slots 28 in tubular member 26 using any of these or other manufacturing steps.

In at least some embodiments, slots 28 may be formed in tubular member using a laser cutting process. The laser cutting process may include essentially any suitable laser and/or laser cutting apparatus. For example, the laser cutting process may utilize a fiber laser. Utilizing processes like laser cutting may be desirable for a number of reasons. For example, laser cutting processes may allow tubular member 26 to be cut into a number of different cutting patterns in a precisely controlled manner. This may include variations in the slot width (which also may be termed "kerf"), annular segment width, beam height and/or width, etc. Furthermore, changes to the cutting pattern can be made without the need to replace the cutting instrument (e.g., a blade). This may also allow smaller tubes (e.g., having a smaller outer diameter) to be used to form tubular member 26 without being limited by a minimum cutting blade size. Consequently, tubular members 20 may be fabricated for use in neurological devices or other devices where a small size may be desired.

Because of the precision and control that may be achieved by cutting slots 28 with a laser, numerous additional variation can be achieved in slot 28 configurations, arrangements, etc. Still referring to FIG. 7, a side view of tubular member 26 is illustrated. Tubular member 26 includes a plurality of annular segments 32 including annular segment 32a, annular segment 32b, and annular segment 32c. In this example, segment 32a is disposed longitudinally-adjacent (i.e., right next to) segment 32b and segment 32c is disposed longitudinally-adjacent segment 32b (oppositely segment 32a). The number of annular segments 32 in a given tubular member 26 may vary depending on the structure of tubular member 26. For example, as the number of slots 28 increases, the number of annular segments 32 may similarly increase. The invention is not intended to be limited to any particular number or arrangement of annular segments 32 for any given tubular member 26 or device including a tubular member 26.

Segments 32a/32b/32c can be understood to be generally circumferential or "round" portions of tubular member 26 that are defined between groups or sets of slots 28. For example, segment 32a is defined between a first group of slots 28a and a second group of slots 28b. Likewise, segment 32b is defined between group 28b and a third group of slots 28c. Moreover, segment 32c is defined between group 28c and a fourth group of slots 28d. In this example, each group 28a/28b/28c/28d includes two slots 28. However, any suitable number of slots 28 may be utilized for any group 28a/28b/ 28c/28d. Just like the annular segments 32, the invention is not intended to be limited to any number of slots 28, groups of slots 28, or number of slots 28 per group for any given tubular member 26 or device including a tubular member 26 with slots 28.

When slots 28 are formed in tubular member 26, a portion of tubular member 26 remains at the longitudinal location where slots 28 are formed and extends between longitudinally-adjacent annular segments 32. This portion is called a "beam" 34. Several beams 34 are illustrated in FIG. 7 including beam 34a, beam 34a', beam 34b, beam 34b', beam 34c, beam 34c', beam 34d, and beam 34d'. Beams 34a/34a'/34b/ 34b'/34c/34c'/34d/34d' can be understood to be portions of tubular member 26 that connects or attaches longitudinally-adjacent annular segments 32. Each pair of longitudinally-adjacent annular segments (e.g., 32a and 32b) is attached by two beams (e.g., 34b and 34b'), which form a beam pair at the same longitudinal location along tubular member 26. Similarly, segment 32b is attached to segment 32c by beams 34c and 34c'. In this example, each group 28a/28b/28c/28d of slots 28 defines or leaves behind two, corresponding beams at a given longitudinal location. In FIG. 7, which illustrates tubular member 26 from the side, one beam (e.g., 34a, 34b, 34c, 34d) of each beam pair can be seen from the front and the other beam (e.g., 34a', 34b', 34c', 34d') of the beam pair can be seen from the back and is shaded for clarity.

Figure 8:
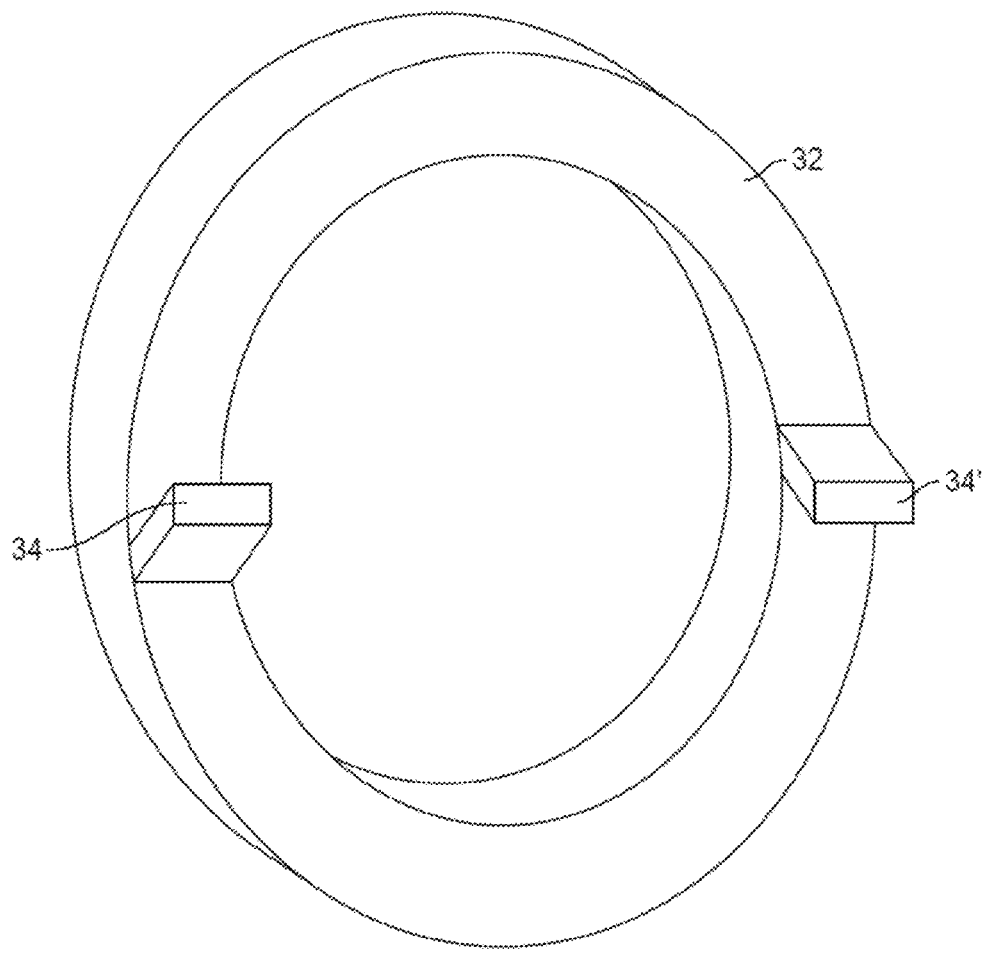
FIG. 8 is a detailed end view of an annular segment and two beams of a balloon support shaft constructed according to one embodiment of the disclosed inventions.

The beams 34, 34' are formed in the tubular member 26 such that they meet the annular segments 32 at an oblique angle, as shown in FIG. 8. Further, each beam pair is formed in the tubular member 26 such that it is rotated about the longitudinal axis of the tubular member 26 from the previous beam pair. In this embodiment, each beam pair is angularly displaced or rotated by about eight degrees from the previous beam pair, resulting in a full rotation about every 45 beam pairs. The beam pairs form a double helix structure along the length of the tubular member 26 because of the oblique angle between beams 34 and annular segments 32, and the angular displacement between beam pairs. These helices, which rotate in the same direction, are shown in FIGS. 2, 3, 5, and 6.

As the angle of rotation between adjacent beams 34 is reduced, the portion of the annular segment 32 between beams 34 shortens until it is non-existent on one side and completely isolated from loading (bending, tension and compression) on the other side. In embodiments having small angles of rotation, such as the one depicted in FIG. 5, the beams 34 for a continuous helix. When such a structure is placed in compression or tension the helical line of beam pairs act as a continuous pair of fibers that effectively prevent length change of the structure. When loaded in tension the fibers are prevented from collapsing inward and straightening by the rib support of the annular segments 32. Conversely, when loaded in compression, the fibers are prevented from buckling individually outward by the annular segments 32.

Figure 6:
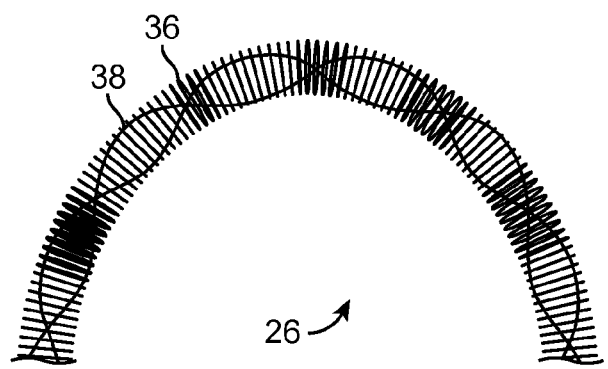
FIG. 6 is a perspective view of the balloon support shaft of FIG. 5 in a bent configuration.

As shown in FIG. 6, the double helix arrangement of beams 34 causes the tubular member 26 to bend in a segmented manner, with more bending occurring in the first region 36 where the beam pair in the helix defines an axis approximately parallel to the plane of bending. Almost no bending in the second region 38 where the beam pair axis is perpendicular to the plane of bending. Increasing the pitch of the helices increases the likelihood that several bending regions 36 will exist in the tightest predicted radius of curvature of the balloon catheter 10. As the angle of rotation between adjacent pairs of beams is increased the helix angle becomes tighter and the tubular member 26 may begin to twist into a ring when bent. The helix angle may be optimized to maximize both axial stiffness and isotropic properties in bending.

Figure 9:
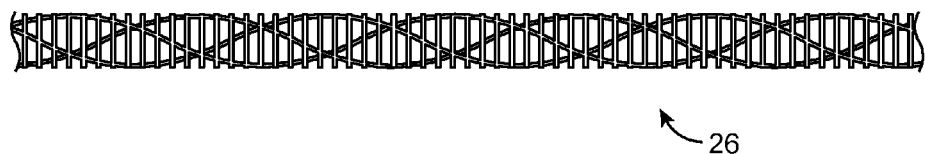
FIG. 9 is a perspective view of a balloon support shaft constructed according to one embodiment of the disclosed inventions.
Figure 10:
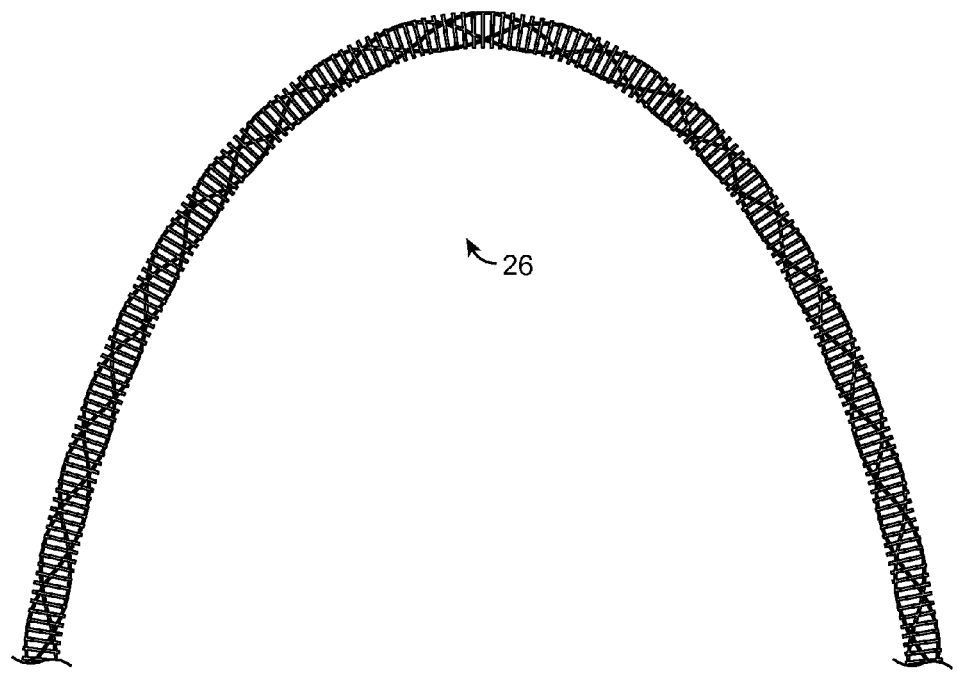
FIG. 10 is a perspective view of the balloon support shaft of FIG. 9 in a bent configuration.

Increasing the number of beams 34 connecting each pair of annular segments 32 results in a tubular member 26 with more isotropic bending. Increasing the number connecting beams 34 from two to three gives the structure a more frequently repeating symmetry along its length. For example, a two beam structure (FIGS. 2, 3, 5, and 6) is symmetric at every 180 degrees of rotation while a three beam structure (FIGS. 9 and 10) is symmetric at every 120 degrees of rotation. The three beam structure will not be as soft as a two beam structure, and may be more useful in proximal regions of the balloon catheter where greater stiffness is desired.

Figure 11:
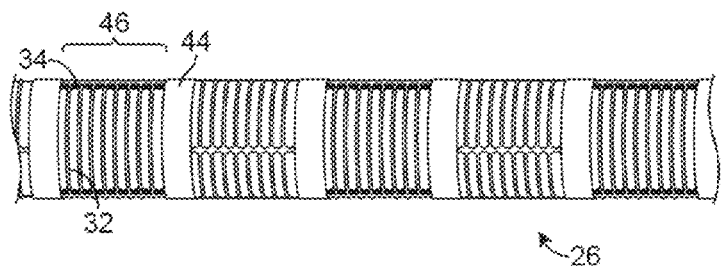
FIG. 11 is a perspective view of a balloon support shaft constructed according to one embodiment of the disclosed inventions.
Figure 12:
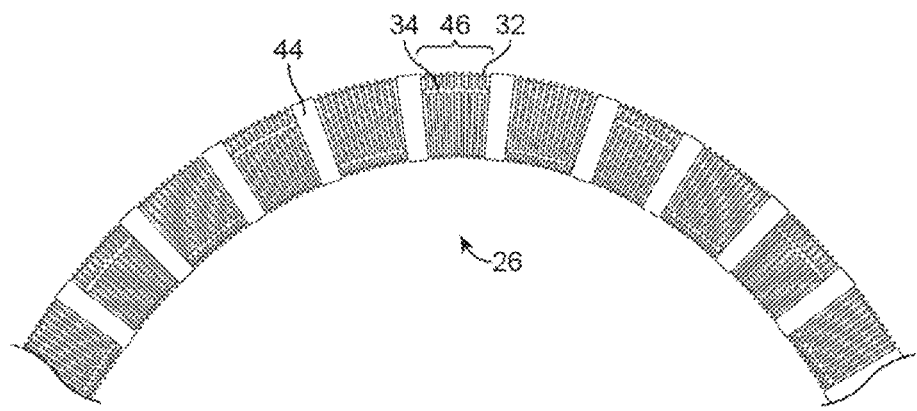
FIG. 12 is a perspective view of the balloon support shaft of FIG. 11 in a bent configuration.

Forming groups 46 of beams 34 and narrow annular segments 32 that are rotated a large increment, such as 90 degrees, from each other where the groups 46 are joined by wider annular segments 44 also results in a more isotropic tubular structure 26. The wider annular segments 44 are wide enough to resist stretching. FIGS. 11 and 12 show one example of such a structure. The beams 34 in each group 46 are all aligned in this example, however they could have a spiral pattern as well.

Just like slot groups 28a/28b/28c, the invention is not intended to be limited to any number of beams 34, groups of beams 34, or number of beams 34 per group for any given tubular member 26 or device including a tubular member 26 with beams 34.

Figure 13A:
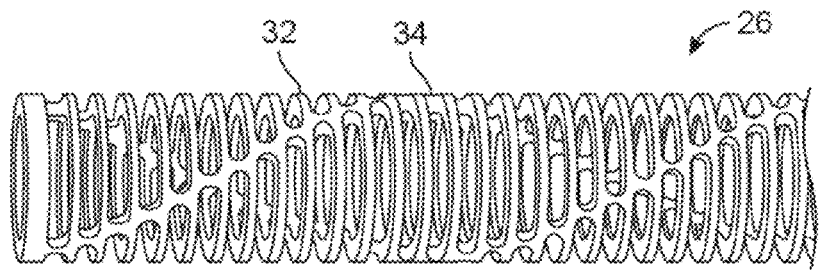
FIGS. 13A-C are detailed perspective views of balloon support shafts according to various embodiments of the disclosed inventions.
Figure 13B:
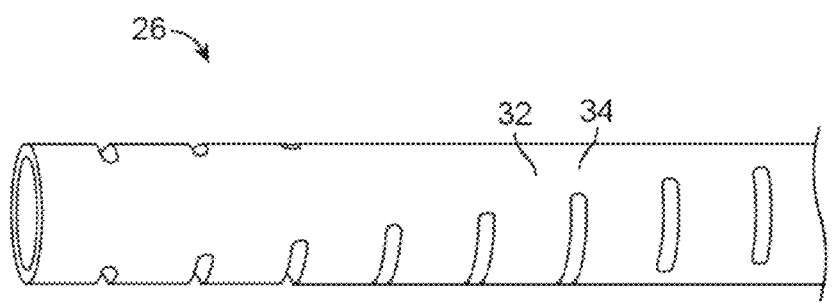
Figure 13C:
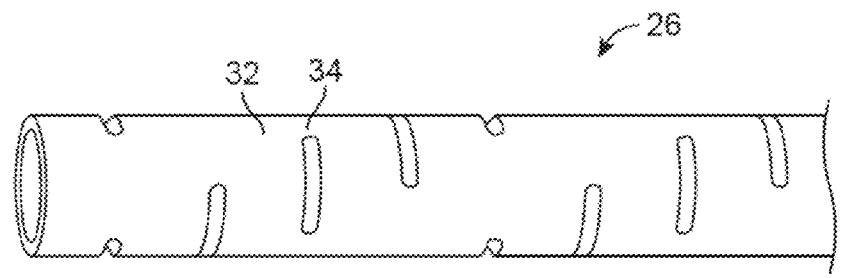

In a typical transvascular device, such as a balloon catheter 10, the proximal region of the device is typically in less tortuous anatomy and the bending stiffness is higher to allow the device to be pushed without bowing or buckling. Accordingly, it is desirable to create a microfabricated structure with stiffness that varies along the length of the device. For instance, the stiffness can decrease and/or increase along the length of the device. The stiffness can also decrease then increase and/or increase then decrease. The stiffness of the structure can be adjusted by increasing the beam 34 and/or annular segment 32 dimensions. These are typically varied at the same time in order to create a structure that has a more uniform distribution of stress. However when the width of the annular segment 32 dimension is increased the pitch of the helix is reduced, so that there are fewer bending regions per length, as shown in FIGS. 13A and 13B. To offset this effect, the rotational angle between beam 34 sets (two, three, or more beams) can be varied proportional to annular segment 32 width to maintain a relatively constant helical pitch along the length of the device. Compare FIGS. 13A and 13B. It can be seen in FIGS. 13A to 13C that as the annular segment 32 width increases the rotational angle can be increased without creating ring structures that will be loaded in bending, tension, or compression. This results in a device with higher bending stiffness and improved pushability and resistance to buckling while still retaining relatively isotropic properties in bending. In other embodiments, annular segment widths and rotational angles can be varied (i.e., increased or decreased).

When the tubular member 26 is used as the center support shaft in a single lumen balloon catheter 10 as shown in FIGS. 1-3, the plurality of slots 28 allows rapid balloon inflation and deflation. The slots 28 are spaced and sized to create an extremely porous structure that allows rapid inflation and deflation from the lumen 30 of the tubular member 26 into the balloon 14. The ease of inflation and deflation enable the use of higher contrast medium, which enhances balloon visibility under fluoroscopy. The slot configuration also provides good axial strength (in tension and compression) as well as kinking and ovalization resistance when navigating tortuous vasculature. Further, tracking of the balloon catheter 10 is improved by varying the bending stiffness of the tubular member 26 such that it is softer at its distal end. Moreover, the tubular member 26 is more resistant to bowing and buckling during balloon inflation and deflation.

During inflation of compliant balloons it is possible for compressive forces to be created along the center shaft of the balloon. Traditional single lumen balloon catheters utilize a plastic shaft with holes drilled in it for fluid passage. The shaft must be stiff enough to resist buckling yet soft enough to track smoothly through tortuous vasculature. A simple plastic tube is not easily modified to vary stiffness along its length and is also susceptible to local buckling. The disclosed structure is highly kink resistant and easily varied in stiffness by changing beam heights, cutwidths, cut spacing, wall thickness, etc. Column buckling (Euler buckling), regardless of end constraints, is linearly proportional to bending stiffness and varies inversely with column length squared. Thus by stiffening the proximal portion of a shaft and softening the distal end, it is possible to create a net gain in buckling strength while retaining a soft distal tip, particularly for longer and larger balloon sizes (critical for atraumatic tracking) Alternatively, softening the stiffness profile of the entire shaft for shorter and smaller balloons to create maximum distal flexibility may provide better tracking.

Tubular member 26 and/or other components of balloon catheter 10 may be made from a metal, metal alloy, polymer (some examples of which are disclosed below), a metal-polymer composite, ceramics, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of tubular member 26 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of balloon catheter 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of balloon catheter 10 to achieve the same result.

In some embodiments, a degree of MRI compatibility is imparted into balloon catheter 10. For example, to enhance compatibility with Magnetic Resonance Imaging (MRI) machines, it may be desirable to make tubular member 26, or other portions of the balloon catheter 10, in a manner that would impart a degree of MRI compatibility. For example, tubular member 26, or portions thereof, may be made of a material that does not substantially distort the image and create substantial artifacts (artifacts are gaps in the image). Certain ferromagnetic materials, for example, may not be suitable because they may create artifacts in an MRI image. Tubular member 26, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

The entire balloon catheter 10 can be made of the same material along its length, or in some embodiments, can include portions or sections made of different materials. In some embodiments, the material used to construct balloon catheter 10 is chosen to impart varying flexibility and stiffness characteristics to different portions of balloon catheter 10. For example, proximal section 18 and distal section 20 of balloon catheter 10 may be formed of different materials, for example materials having different moduli of elasticity, resulting in a difference in flexibility. In some embodiments, the material used to construct proximal section 18 can be relatively stiff for pushability and torqueability, and the material used to construct distal section 20 can be relatively flexible by comparison for better lateral trackability and steerability. For example, proximal section 18 can be formed of polyimide shaft and/or doped polytetrafluoroethylene (PTFE) reinforced with 304v stainless steel wire or ribbon variable pick braiding or variable pitch cross wounding and distal section 20 can be formed with multi-durometer polymeric outer jacket such as PEBAX® over variable pick/pitch reinforced structure.

In embodiments where different portions of balloon catheter 10 are made of different materials, the different portions can be connected using any suitable connecting techniques and/or with a connector. For example, the different portions of balloon catheter 10 can be connected using welding (including laser welding/bonding), soldering, brazing, adhesive, thermal bonding or the like, or combinations thereof. These techniques can be utilized regardless of whether or not a connector is utilized. The connector may include any structure generally suitable for connecting portions of a balloon catheter. One example of a suitable structure includes a structure such as a hypotube or a coiled wire which has an inside diameter sized appropriately to receive and connect to the ends of the proximal portion and the distal portion. Essentially any suitable configuration and/or structure can be utilized for connecting various portions of the balloon catheter 10 including those connectors described in U.S. Pat. Nos. 6,918,882 and 7,071,197 and/or in U.S. Patent Pub. No. 2006-0122537, the entire disclosures of which are herein incorporated by reference.

As shown in FIG. 7, a polymer jacket 40 is laminated over the tubular member 26. The polymer jacket 40 may be disposed over portions or all of the tubular member 26 that may define a generally smooth outer surface for balloon catheter 10. In other embodiments, however, such a jacket 40 or covering may be absent from a portion or all of balloon catheter 10, such that the tubular member 26 may form the outer surface. The jacket 40 may be made from a polymer or any other suitable material. Some examples of suitable polymers may include low density polyethylene (LDPE), linear low density polyethylene (LLDPE), polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the jacket 40 can be blended with a liquid crystal polymer (LCP). For example, the mixture can contain up to about 6% LCP.

In some embodiments, the exterior surface of the balloon catheter 10 (including, for example, the exterior surface of the tubular member 26) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the jacket 40, or in embodiments without a jacket over portion of the tubular member, or other portions of device 10. Alternatively, the jacket 40 may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The jacket 40 may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The jacket 40 may be impregnated with radiopaque filler materials such as barium sulfate, bismuth, or tungsten to facilitate radiographic visualization. Those skilled in the art will recognize that these materials can vary widely without deviating from the scope of the present invention.

The distal portion of the balloon 14 is attached to the distal end of the tubular member 26 and to the distal flexible tip distal of the inflation ports/irrigation channels. The balloon 14 is positioned on the tubular member 26 such that the balloon 14 overlies the portion of the tubular member 26 having slots 28 formed therein. The balloon 14 may be made of a highly compliant material that elastically expands upon pressurization. Because the balloon 14 elastically expands from the deflated state to the inflated state, the balloon 14 has an extremely low profile in the deflated state and may be used without folding the balloon. The balloon may be formed of silicone, urethane polymer, or an extruded thermoplastic elastomers polyisoprene rubber such as a 70A, 65A, 60A, 52A, 45A, 42A, 40A, 32A, 30A, 25A, 15A, 12A, and 5A durometer hydrogenated polyisoprene rubber, which is commercially available under the trade name Chronoprene™ and Mediprene™ from AdvanSource Biomaterials, Inc. and Elasto, respectively. Hydrogenated polyisoprene provides a balloon having superior performance and manufacturing attributes. In particular, hydrogenated polyisoprene may be processed with standard polyolefin processing equipment to obtain balloon tubing having a wall thickness of approximately 0.001 inches to 0.010 inches and a corresponding inside diameter of approximately 0.016 inches to 0.058 inches. Such tubing produces balloons having a nominal inflated outside diameter of approximately 3.0 mm to 7.5 mm. The highly compliant balloon preferably elastically expands at pressures less than 1.0 ATM. The highly compliant balloon may have a pressure compliance of 2.0 mm/ATM or more at pressures less than 2.0 ATM. The highly compliant balloon may have a volumetric compliance of approximately 0.3 mm per 0.01 ml to 0.5 mm per 0.01 ml at pressures less than 2.0 ATM, for balloons having a nominal diameter of approximately 3.5 mm and a length of approximately 10 mm to 30 mm. The ends of the balloon are attached to the tubular member 26 and the flexible distal tip using conventional bonding means such as thermal bonding using a hot jaw, hot air source, or a laser. The tubular member 26, excluding the balloon 14 and distal flexible tip, can be coated with hydrophilic coatings such as Hydropass, Hydrolene or Bioslide.

Figure 4:
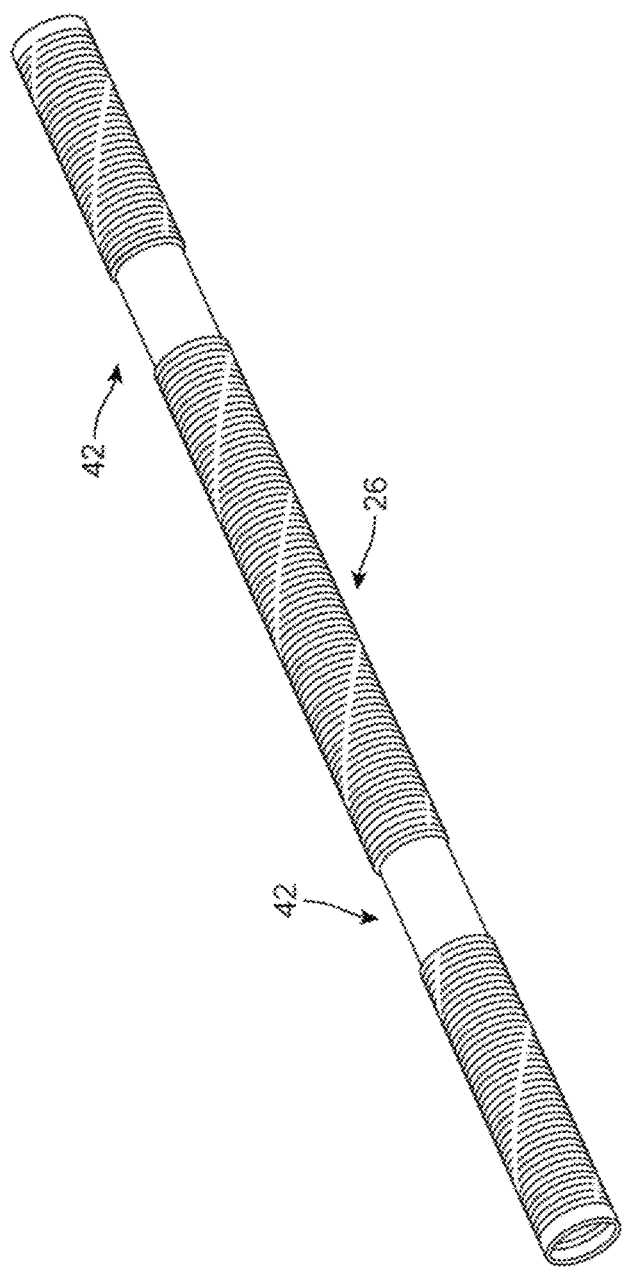
FIG. 4 is a perspective view of a balloon support shaft constructed according to one embodiment of the disclosed inventions.
Figure 5:
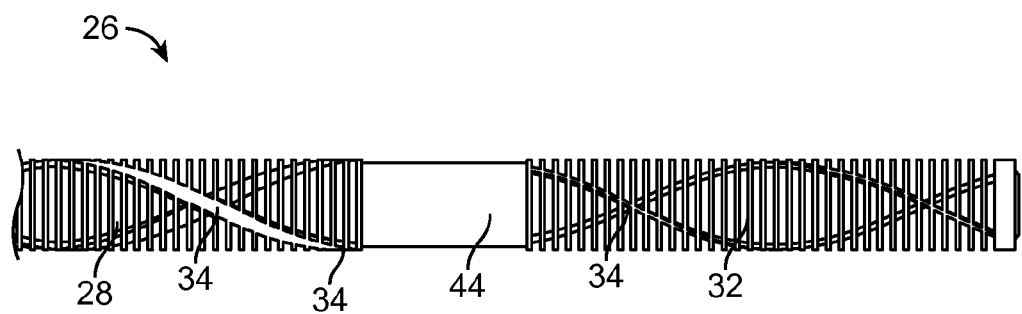
FIG. 5 is a perspective view of a balloon support shaft constructed according to one embodiment of the disclosed inventions.

As shown in FIG. 4, marker bands 42 are mounted on the tubular member 26. FIG. 5 shows the recessed wide annular segment 44 configured to hold the cylindrical marker band 42 in FIG. 4. Further, the annular segments 32 on either side of the recessed wide annular segment 44 are raised relative to the recessed wide annular segments 44 (not beyond the outer diameter of the tubular member 26) to retain the marker band 42 therein. The marker band 42 may be made of a full band, slit band, or coil wound of round or ribbon wire made of materials like Platinum/Tungsten, Gold. The marker band 42 may also be made from a low durometer polymer or any other suitable materials impregnated with radiopaque filler materials such as Barium Sulfate, Bismuth or Tungsten to facilitate radiographic visualization. Some examples of suitable polymers may include low density polyethylene (LDPE), linear low density polyethylene (LLDPE), elastomeric polyamides, block polyamide/ethers, polyether block amide (PEBA, for example available under the trade name PEBAX®).

Figure 14:
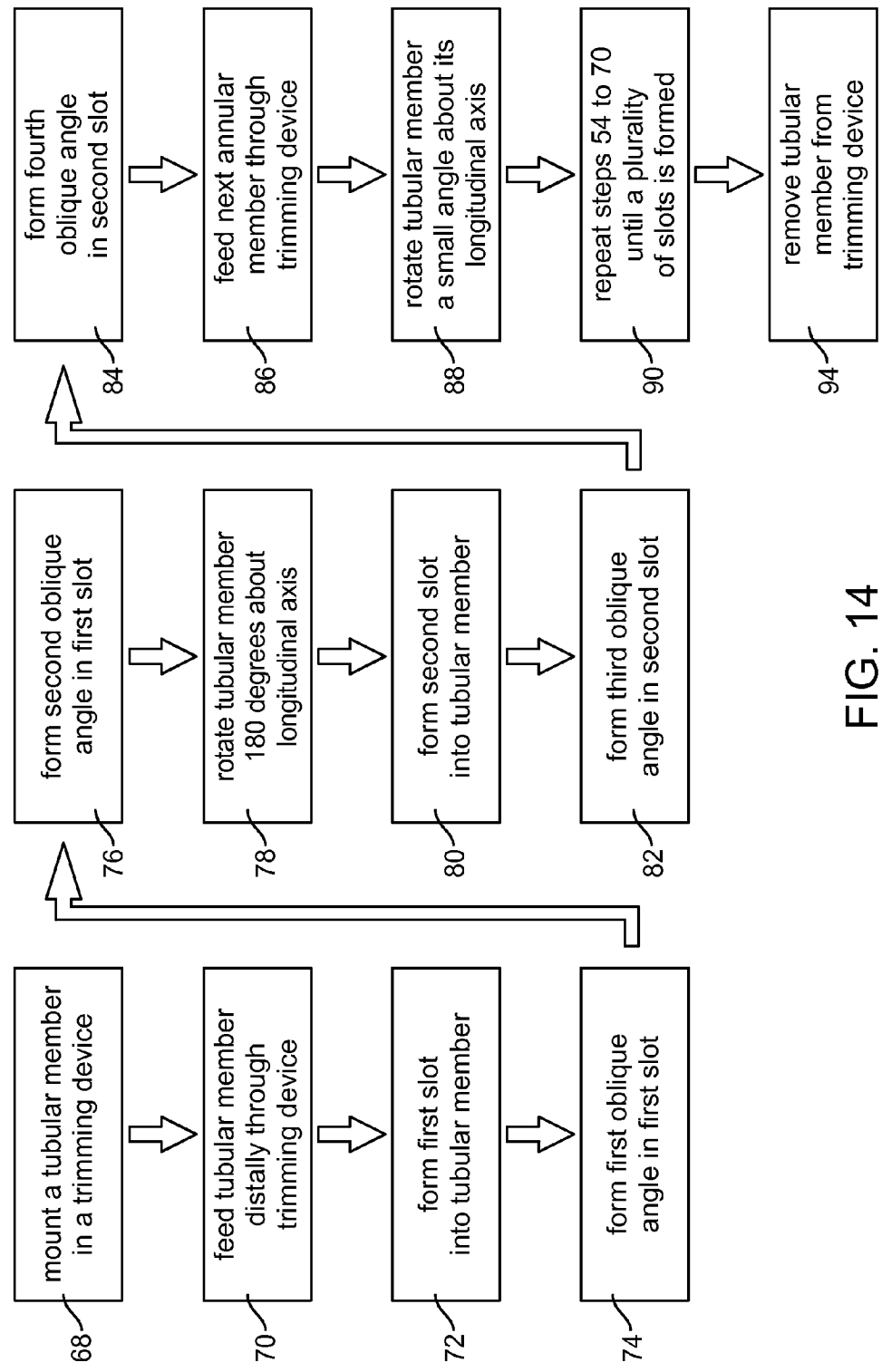
FIG. 14 is a flow chart showing a method of manufacturing a balloon support shaft according to one embodiment of the disclosed inventions.

As shown in FIG. 14, a balloon catheter 10 may be manufactured by first mounting a tubular member 26 in a trimming device (step 68). Next, a first annular segment 32 of the tubular member 26 is fed distally through the trimming device (step 70). Then, a first slot 28 is formed into the tubular member 26 proximal of the first annular segment 32, e.g. by laser cutting (step 72). Subsequently, a first oblique angle is formed at a first end of the first slot 28 (step 74).

Next, a second oblique angle, perpendicular to the first oblique angle, is formed at a second end of the first slot 28 (step 76). Then, the tubular member 26 is rotated 180 degrees about its longitudinal axis (step 78). Subsequently, a second slot 28 is formed into the tubular member 26 proximal of the first annular segment 32 (step 80).

Next, a third oblique angle is formed at a first end of the second slot 28 (step 82). Then, a fourth oblique angle, perpendicular to the first oblique angle, is formed at a second end of the second slot 28 (step 84). Subsequently, the next annular segment 32 of the tubular member 26 is fed distally through the cutting device (step 86).

Next, tubular member is rotated a small angle (about eight degrees) about its longitudinal axis (step 88). Step 72 to step 88 are repeated until a plurality of slots 28 have been cut into the tubular member 26 (step 90), at which time the tubular member 26 is removed from the trimming device (step 92). In some embodiments, the tubular member 26 is covered with a polymer jacket 40.

Finally, when making a balloon catheter 10, a balloon 14 is attached to the tubular member 26 so that the balloon 14 defines a lumen in communication with at least one slot 28.

FIG. 15 depicts a balloon catheter 10 having a balloon support shaft 24 with slots 28 formed therein and a balloon 14 overlying the balloon support shaft 24. The balloon 14 may be made of ChronoPrene™ and the balloon support shaft may be a nitinol tube with slots 28 micro-machined therein. The proximal and distal ends 46, 48 of the balloon 14 overly proximal and distal sections 50, 52 of the balloon support shaft 24, respectively. As a result of the manufacturing process, the proximal and distal sections 50, 52 of the balloon support shaft 24 are covered by a polymer (e.g., polyethylene) jacket 40, creating proximal and distal spaces 54, 56 in the balloon 14. These spaces 54, 56 are "dead" in the hydrodynamic sense because they fluids cannot flow through the spaces 54, 56 without changing direction. Consequently, as the balloon catheter 10 is being flushed, air bubbles collect and/or become trapped in the proximal and distal spaces 54, 56 as described above. Pressure in the balloon catheter 10 drops in a distal direction along the longitudinal axis of the balloon catheter 10. Accordingly, most air bubbles migrate to the distal space 56. The air bubbles may be 1 mm or larger and may lead to complications such as imaging difficulties and air emboli. The balloon catheter 10 also includes marker bands 42 inside of the balloon 14 that are also covered with the polymer jacket 40 and increase the size of the dead spaces 54, 56.

Figure 17:
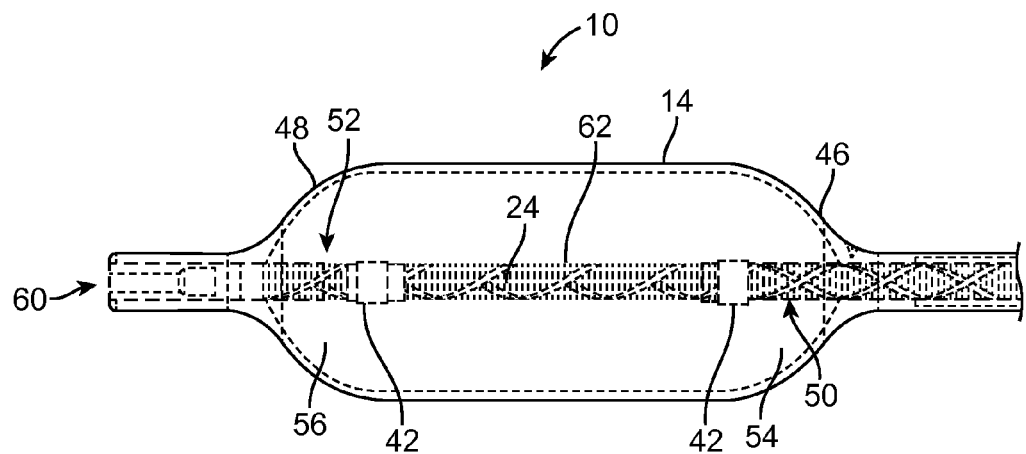
FIG. 17 is a detailed side schematic view of the distal portion of a balloon catheter according to yet another embodiment of the disclosed inventions, with the balloon shown as transparent to depict the elements contained therein.
Figure 18:
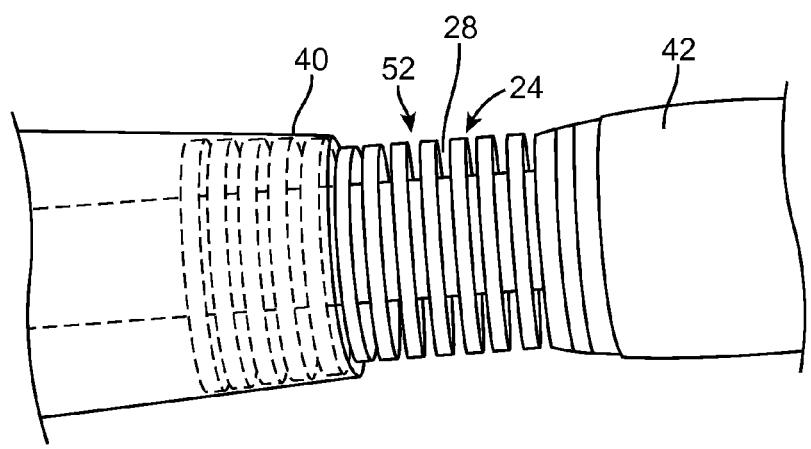
FIG. 18 is a detailed side schematic view of the distal portion of a balloon catheter according to yet another embodiment of the disclosed inventions.

FIGS. 16-18 depict a balloon catheter 10 similar to the one depicted in FIG. 15. In this embodiment, the distal section 52 of the balloon support shaft 24, which underlies the distal end 48 of the balloon 14 and the distal space 56, is not covered by a polymer jacket 40. Accordingly, the slots 28 in the distal section 52 of the balloon support shaft 24 allow communication between the interior 58 of the balloon 14 and the lumen 30 of the balloon support shaft 24. Any air bubbles that collect and/or become trapped in the distal space 56 may be flushed out of the distal space 56 by fluid flowing from the interior 58 of the balloon 14 and the lumen 30 of the balloon support shaft 24. From the lumen 30, the air bubbles can be harmlessly flush out of a distal opening 60 at the distal end of the balloon support shaft 24. Such fluid may be introduced from an inflation source 22 attached to the proximal end of the balloon catheter 10, through the slots 28 in a middle section 62 of the balloon support shaft 24, and into the interior 58 of the balloon 14.

As shown in FIG. 18, the slots 28 in the distal section 52 of the balloon support shaft 24 extend completely around the circumference of the balloon support shaft 24. This design allows collected and/or trapped air bubbles, which may be located anywhere on the circumference of the balloon support shaft 24, to be flushed from the interior 58 of the balloon 14 via the slots 28 in the distal section 52. This design also increases the flexibility and trackability of the distal portion 20 of the elongate member 16 of the balloon catheter 10.

FIG. 19 depicts an alternative embodiment of a balloon catheter 10 similar to the one depicted in FIGS. 16-18. In this embodiment, the proximal section 50 of the balloon support shaft 24, which underlies the proximal end 46 of the balloon 14 and the proximal space 54, is also not covered by the polymer jacket 40, like the distal section 52 of the balloon support shaft 24. This design allows air bubbles that collect and/or become trapped in the proximal space 54 to be flushed out of the proximal space 54, into the lumen 30, and out of the distal opening 60 of the balloon support shaft 24, as described above. Air bubbles tend to collect and/or become trapped in the proximal space 54 in larger diameter compliant and super compliant balloons 14.

FIG. 20 depicts another alternative embodiment wherein flow out of the proximal and distal spaces 54, 56 is increased by forming slots 28 in the marker bands 42 that are at least partially aligned with the slots 28 in the balloon support shaft 24 underlying the marker bands 42. The slots 28 in the marker bands 42 allow flow through the bands, thereby increasing the ability to flush air bubbles from the proximal and distal spaces 54, 56, as described above. The slots 28 in the marker bands 42 also increase the flexibility and trackability of the distal portion 20 of the elongate member 16 of the balloon catheter 10. In still another embodiment (not shown), the slotted marker band 42 is replaced with a radiopaque coil having a large pitch wherein openings in the coil are at least partially aligned with the slots 28 in the balloon support shaft 24 underlying the coil.

Figure 22:
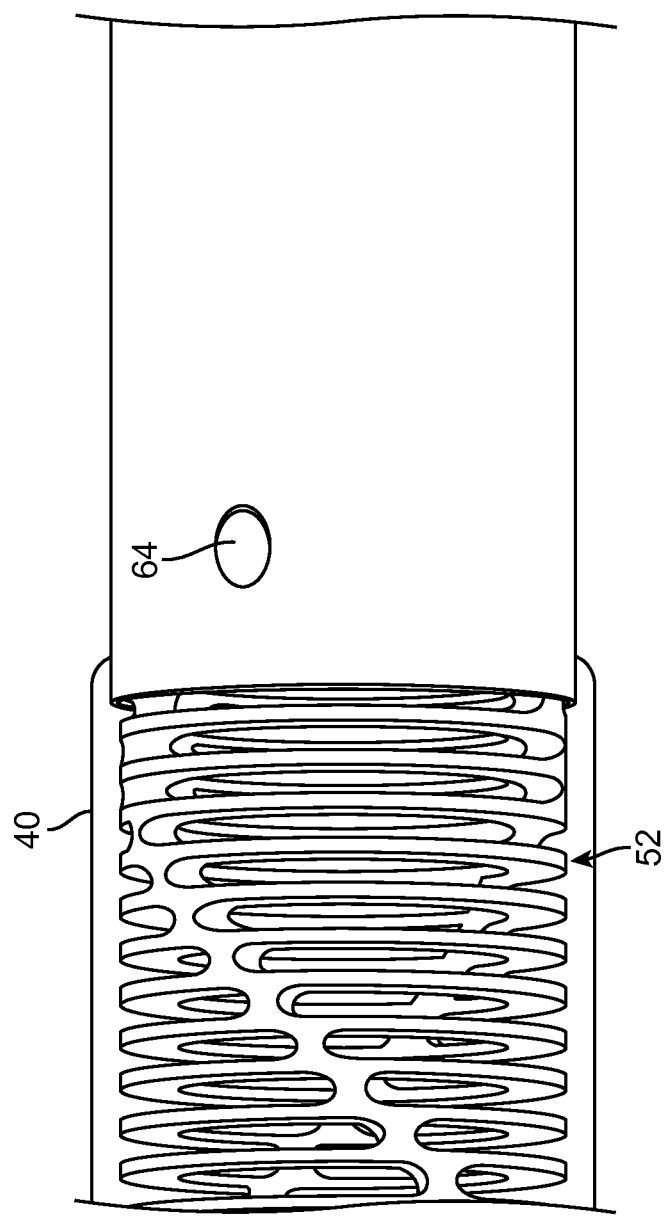

FIGS. 21 and 22 depict yet another alternative embodiment wherein instead of open slots 28 being formed in the distal section 52 of the balloon support shaft 24, a vent hole 64 is formed in the distal section 52, e.g., by laser drilling. The vent hole 64 allows air bubbles that collect and/or become trapped in the distal space 56 to be flushed out of the distal space 56, into the lumen 30, and out of the distal opening 60 of the balloon support shaft 24, as described above.

To prepare a balloon catheter 10, such as the one depicted in FIGS. 16-18, for use, the balloon catheter 10 is first flushed. Fluid is introduced into the lumen 30 of the balloon support shaft 24 from an inflation source 22 attached to the proximal end of the balloon catheter 10. Pressure from the inflation source 22 drives the fluid from the lumen 30, through the slots in the middle section 62 of the balloon support shaft 24, and into the balloon 14. As the fluid travels through the balloon catheter 10, it drives the air out of the balloon catheter 10. However, some air may be trapped in the system as air bubbles. These bubbles tend to collect and/or become trapped in the annular space between the inner surface of the balloon 14 and the outer surface of the balloon support shaft 24, and more particularly in the distal space 56 in the balloon 14.

The fluid travels through the interior 58 of the balloon 14 and exits through the slots 28 in the distal section 52 of the balloon support shaft 24, and back into the lumen 30. As the fluid exits through the slots 28 in the distal section 52, it carries any trapped air bubbles from the distal space 56 into the balloon support shaft lumen 30. From the balloon support shaft lumen 30, the fluid and the air bubbles are flushed out of the distal opening 60 of the balloon support shaft 24.

After flushing, the balloon 14 is inflated by closing the distal opening 60 and visually inspected for air bubbles. The balloon 14 may be inflated by advancing a guidewire past the distal opening 60 to occlude and seal against an annular tip seal 66 disposed in the lumen 30 of the balloon support shaft 24 distal of the distal section 52. Occluding and sealing against the annular tip seal 66 allows the balloon 14 to inflate through the slots 28 in the balloon support shaft 24. The annular tip seal 66 may be made of ChronoPrene™ 70A, 65A, 60A, 52A, 45A, 42A, 40A, 32A, 30A, 25A, 15A, 12A, or 5A durometer. If an unacceptable amount of air bubbles (of a certain size) is identified in the balloon 14 after inflation, the balloon catheter 10 is flushed again until the amount of air bubbles identified in the inflated balloon 14 is acceptable.

What is claimed is:

1. A balloon catheter, comprising:
   an elongate support member comprising a tubular wall defining first and second openings therein, open proximal and distal ends, and an axial lumen in communication with the first and second openings and the open proximal and distal ends; and
   a balloon disposed on the elongate support member, the balloon defining a balloon interior through which the elongate support member extends,
   wherein the balloon interior has a proximal end region, a middle region, and a distal end region, with the first opening located in the middle region, and the second opening located in the distal end region, such that the support member lumen is in communication with the balloon interior through each of the first and second openings, and such that a pressurized liquid introduced through the open proximal end of the support member will enter the balloon interior through the first opening, and subsequently exit the balloon interior through the second opening, back into the lumen, and out the open distal end of the support member, and
   wherein a radipaque marker is disposed on the elongate support member in the distal end region of the balloon interior, proximal of the second opening.

2. The balloon catheter of claim 1, wherein the second opening is a slot defined by the elongate support member.

3. A balloon catheter, comprising:
   an elongate support member comprising a tubular wall defining first and second openings therein, open proximal and distal ends, and an axial lumen in communication with the first and second openings and the open proximal and distal ends;
   a balloon disposed on the elongate support member, the balloon defining a balloon interior through which the elongate support member extends,
   wherein the balloon interior has a proximal end region, a middle region, and a distal end region, with the first opening located in the middle region, and the second opening located in the distal end region, such that the support member lumen is in communication with the balloon interior through each of the first and second openings, and such that a pressurized liquid introduced through the open proximal end of the support member will enter the balloon interior through the first opening, and subsequently exit the balloon interior through the second opening, back into the lumen, and out the open distal end of the support member; and
   a radiopaque marker disposed in the balloon interior on the elongate support member between the first opening and the second opening, the radiopaque marker comprising a marker tubular wall defining a marker opening therein, wherein the tubular wall of the elongate support member also defines a third opening therein at least partially underlying the marker opening, such that the support member lumen is in communication with the balloon interior through the third opening and the marker opening.

4. The balloon catheter of claim 3, the radiopaque marker comprising an open pitch coil.

5. The balloon catheter of claim 1, wherein the elongate support member is a metal hypotube, and the first and second openings are micro-machined therein.

6. The balloon catheter of claim 1, wherein the elongate support member is a polymeric tube, and the first and second openings are drilled therein.

7. The balloon catheter of claim 1, wherein the elongate support member further comprises a polymeric sleeve disposed around a portion of the elongate support member, and wherein the portion of the elongate support member in which the second opening is formed is free of the polymeric sleeve.

8. The balloon catheter of claim 1, wherein the elongate support member further comprises an annular seal disposed in the lumen distal of the balloon.

9. The balloon catheter of claim 1, wherein the tubular wall also defines a third opening located in the proximal end region, such that the support member lumen is in communication with the balloon interior through the third opening, and such that a pressurized liquid introduced into the open proximal end of the support member will enter the balloon interior through the first opening, and subsequently exit the balloon interior through the second and third openings, back into the lumen, and out the open distal end of the support member.

10. The balloon catheter of claim 9, wherein the balloon comprises a compliant or super compliant material.

11. A balloon catheter, comprising:
an elongate support member comprising a tubular wall defining first, second, and third slot-shaped openings therein, open proximal and distal ends, and an axial lumen in communication with the first, second, and third openings and the open proximal and distal ends; and
a balloon disposed on the elongate support member, the balloon defining a balloon interior surrounding a portion of the elongate support member,
wherein the balloon interior has a proximal end region, a middle region, and a distal end region, with the first opening located in the middle region, the second opening located in the distal end region, and the third opening located in the proximal end region, such that the support member lumen is in communication with the balloon interior through each of the first, second, and third openings, and such that a pressurized liquid introduced through the open proximal end of the support member will enter the balloon interior through the first opening, and subsequently exit the balloon interior through the second and third openings, back into the lumen, and out the open distal end of the support member,
wherein a radiopaque marker is disposed on the elongate support member in the distal end region of the balloon interior, proximal of the second opening.

12. The balloon catheter of claim 11, the radiopaque marker comprising a marker tubular wall defining a marker opening therein, wherein the tubular wall of the elongate support member also defines a fourth opening therein at least partially underlying the marker opening, such that the support member lumen is in communication with the balloon interior through the fourth opening and the marker opening.

13. The balloon catheter of claim 12, the radiopaque marker comprising an open pitch.

14. The balloon catheter of claim 11, wherein the elongate support member further comprises a polymeric sleeve disposed around a portion of the elongate support member, and wherein the portions of the elongate support member in which the second and third openings are formed are free of the polymeric sleeve.

15. The balloon catheter of claim 11, wherein the elongate support member further comprises an annular seal disposed in the lumen distal of the balloon.

16. The balloon catheter of claim 11, wherein the balloon comprises a compliant or super compliant material.

\* \* \* \* \*